US009364634B2

(12) United States Patent
Adams et al.

(10) Patent No.: US 9,364,634 B2
(45) Date of Patent: Jun. 14, 2016

(54) SYSTEMS AND METHODS FOR IMPROVING CATHETER HOLE ARRAY EFFICIENCY

(75) Inventors: Chad M. Adams, Cedar Hills, UT (US); Jonathan Karl Burkholz, Salt Lake City, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 717 days.

(21) Appl. No.: 13/248,483

(22) Filed: Sep. 29, 2011

(65) Prior Publication Data
US 2012/0022502 A1   Jan. 26, 2012

Related U.S. Application Data

(63) Continuation-in-part of application No. 12/427,633, filed on Apr. 21, 2009, now Pat. No. 8,403,911.

(60) Provisional application No. 61/388,646, filed on Oct. 1, 2010, provisional application No. 61/046,843, filed on Apr. 22, 2008.

(51) Int. Cl.
*A61M 25/00*   (2006.01)

(52) U.S. Cl.
CPC ......... *A61M 25/0009* (2013.01); *A61M 25/007* (2013.01); *A61M 25/0015* (2013.01); *A61M 2025/0073* (2013.01); *Y10T 29/49885* (2015.01)

(58) Field of Classification Search
CPC ................ A61M 2025/0073; A61M 25/0009; A61M 25/0015; A61M 25/007; Y10T 29/49885

USPC ............... 604/523–532, 95.01–95.05; 29/428
See application file for complete search history.

(56) References Cited

U.S. PATENT DOCUMENTS

| 2,972,779 A | 2/1961 | Cowley |
| 3,713,442 A | 1/1973 | Walter |

(Continued)

FOREIGN PATENT DOCUMENTS

| CA | 1323537 C | 10/1993 |
| EP | 0 299 622 A2 | 6/1988 |

(Continued)

OTHER PUBLICATIONS

Weber, Paul W. et al., "AJR: Modified Catheter Can Reduce Contrast Material Injuries," Health Imaging.com, Clinical Studies, http://www.healthimaging.com/index.php?view=article&id=18807%3Aajr-modified-cath . . . , 1 page, Oct. 21, 2009.

(Continued)

*Primary Examiner* — Imani Hayman
(74) *Attorney, Agent, or Firm* — Jeanne Lukasavage; Craig Metcalf; Kirton McConkie

(57) ABSTRACT

Peripheral catheters having diffusion holes can be reinforced by embedding stripe material within the material of the catheter tube body. The stripe material can be embedded using a coextrusion process. The stripe material may consist of one or more stripes which may be arranged in a straight or non-linear pattern such as a helical pattern. The diffusion holes can be positioned between adjacent stripes or between adjacent portions of a single stripe. The diffusion holes can be formed after the stripe material has been embedded. A lubricant may be applied to a peripheral catheter that includes stripe material and diffusion holes.

20 Claims, 11 Drawing Sheets

(56) References Cited

U.S. PATENT DOCUMENTS

| | | | |
|---|---|---|---|
| 3,828,767 A * | 8/1974 | Spiroff | 600/435 |
| 4,173,981 A * | 11/1979 | Mortensen | 604/8 |
| 4,292,270 A | 9/1981 | Hannah et al. | |
| 4,330,497 A | 5/1982 | Agdanowski | |
| 4,563,180 A | 1/1986 | Jervis et al. | |
| 4,639,246 A | 1/1987 | Dudley | |
| 4,657,024 A * | 4/1987 | Coneys | 600/435 |
| 4,661,094 A | 4/1987 | Simpson | |
| 4,717,381 A | 1/1988 | Papantonakos | |
| 4,770,652 A | 9/1988 | Mahurkar | |
| 4,784,638 A | 11/1988 | Ghajar et al. | |
| 4,863,441 A | 9/1989 | Lindsay et al. | |
| 4,961,731 A | 10/1990 | Bodicky et al. | |
| 4,968,307 A | 11/1990 | Dake et al. | |
| 5,037,403 A | 8/1991 | Garcia | |
| 5,085,635 A | 2/1992 | Cragg | |
| 5,088,991 A | 2/1992 | Weldon | |
| 5,201,723 A | 4/1993 | Quinn | |
| 5,221,257 A * | 6/1993 | Rosenbloom et al. | 604/510 |
| 5,234,406 A | 8/1993 | Drasner et al. | |
| 5,250,034 A | 10/1993 | Appling et al. | |
| 5,267,979 A | 12/1993 | Appling et al. | |
| 5,334,154 A | 8/1994 | Samson et al. | |
| 5,380,307 A | 1/1995 | Chee et al. | |
| 5,507,751 A | 4/1996 | Goode et al. | |
| 5,536,261 A | 7/1996 | Stevens | |
| 5,542,925 A | 8/1996 | Orth | |
| 5,578,006 A | 11/1996 | Schön | |
| 5,616,137 A | 4/1997 | Lindsay | |
| 5,647,846 A | 7/1997 | Berg et al. | |
| 5,662,619 A | 9/1997 | Zarate | |
| 5,725,495 A | 3/1998 | Strukel et al. | |
| 5,782,811 A | 7/1998 | Samson et al. | |
| 5,830,181 A | 11/1998 | Thornton | |
| 5,843,017 A | 12/1998 | Yoon | |
| 5,857,464 A | 1/1999 | Desai | |
| 5,876,383 A | 3/1999 | Grooters et al. | |
| 5,976,114 A | 11/1999 | Jonkman et al. | |
| 6,052,612 A | 4/2000 | Desai | |
| 6,129,700 A | 10/2000 | Fitz | |
| 6,132,405 A | 10/2000 | Nilsson et al. | |
| 6,197,014 B1 * | 3/2001 | Samson et al. | 604/524 |
| 6,293,958 B1 | 9/2001 | Berry et al. | |
| 6,514,236 B1 | 2/2003 | Stratienko | |
| 6,547,769 B2 | 4/2003 | VanTassel et al. | |
| 6,641,564 B1 | 11/2003 | Kraus | |
| 6,669,679 B1 | 12/2003 | Savage et al. | |
| 6,866,655 B2 | 3/2005 | Hackett | |
| 6,986,752 B2 | 1/2006 | McGuckin, Jr. et al. | |
| 7,077,829 B2 | 7/2006 | McGuckin, Jr. et al. | |
| 7,108,674 B2 | 9/2006 | Quinn | |
| 7,686,800 B2 * | 3/2010 | Savage et al. | 604/528 |
| 7,799,014 B2 | 9/2010 | McGuckin, Jr. et al. | |
| 8,684,967 B2 | 4/2014 | Engel et al. | |
| 2002/0072712 A1 | 6/2002 | Nool et al. | |
| 2003/0023200 A1 | 1/2003 | Barbut et al. | |
| 2004/0030319 A1 | 2/2004 | Korkor et al. | |
| 2004/0158211 A1 * | 8/2004 | Rogers et al. | 604/284 |
| 2005/0124969 A1 | 6/2005 | Fitzgerald et al. | |
| 2005/0197633 A1 | 9/2005 | Schwartz et al. | |
| 2006/0027063 A1 | 2/2006 | Currier et al. | |
| 2006/0184048 A1 | 8/2006 | Saadat | |
| 2006/0189959 A1 | 8/2006 | Schneiter | |
| 2007/0073271 A1 | 3/2007 | Brucker et al. | |
| 2007/0100298 A1 | 5/2007 | Appling | |
| 2007/0197856 A1 | 8/2007 | Gellman et al. | |
| 2007/0255230 A1 | 11/2007 | Gross et al. | |
| 2007/0276354 A1 * | 11/2007 | Osborne | 604/527 |
| 2009/0187141 A1 | 7/2009 | Lareau et al. | |
| 2009/0287186 A1 | 11/2009 | Adams et al. | |
| 2010/0152698 A1 | 6/2010 | Koehler | |
| 2010/0286657 A1 | 11/2010 | Heck | |

FOREIGN PATENT DOCUMENTS

| | | |
|---|---|---|
| EP | 0 947 211 A2 | 10/1999 |
| JP | S63-71049 U | 5/1988 |
| JP | H04221571 A | 8/1992 |
| JP | H10-509071 A | 9/1998 |
| JP | H10-323386 A | 12/1998 |
| JP | H11-513293 A | 11/1999 |
| JP | H11-332990 A | 12/1999 |
| JP | 2000506051 A | 5/2000 |
| JP | 2001-170182 | 6/2001 |
| JP | 2002-519095 A | 7/2002 |
| WO | 93/23105 | 11/1993 |
| WO | WO 99/37341 | 7/1999 |
| WO | WO 01/51116 A2 | 7/2001 |
| WO | WO 01/91830 A1 | 12/2001 |
| WO | WO 2009/052506 A1 | 4/2009 |
| WO | WO 2009/132065 A1 | 10/2009 |

OTHER PUBLICATIONS

Weber, Paul W. et al., "AJR: Modifying Peripheral IV Catheters with Side Holes and Side Slits Results in Favorable Changes in Fluid Dynamic Properties During the Injection of Iodinated Contrast Material," pp. 970-977, AJR:193, Oct. 2009.

* cited by examiner

SYSTEMS AND METHODS FOR IMPROVING CATHETER HOLE ARRAY EFFICIENCY

RELATED APPLICATIONS

This application claims the benefit of U.S. Provisional Application No. 61/388,646, filed Oct. 1, 2010, entitled PIVC DIFFUSION TIP WITH PRE-TIPPING DIFFUSION HOLES/SLOTS CONSTRUCTION, and further is a continuation-in-part of U.S. patent application Ser. No. 12/427,633, filed Apr. 21, 2009, now U.S. Pat. No. 8,403,911 entitled SYSTEMS AND METHODS FOR IMPROVING CATHETER HOLE ARRAY EFFICIENCY, which claims the benefit of U.S. Provisional Application No. 61/046,843, filed Apr. 22, 2008, entitled POWER PIVC HOLE ARRAY EFFICIENCY IMPROVEMENTS, each of which is incorporated herein by reference.

BACKGROUND OF THE INVENTION

The present invention relates generally to vascular infusion systems and components, including catheter assemblies and devices used with catheter assemblies. In particular, the present invention relates to systems and methods for improving catheter hole array efficiency to provide enhanced infusion flowrates, lower system pressures, and reduced catheter exit jet velocities.

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused either from actual blood loss or from internal fluid imbalance. In these clinical settings, it is frequently necessary to infuse blood and/or other fluid rapidly into a patient to avert serious consequences.

Additionally, the ability to inject large quantities of fluid in a rapid manner may be desirable for certain other medical and diagnostic procedures. For example, some diagnostic imaging procedures utilize contrast media enhancement to improve lesion conspicuity in an effort to increase early diagnostic yield. These procedures necessitate viscous contrast media be injected by a specialized "power injector" pump intravenously at very high flow rates, which establishes a contrast bolus or small plug of contrast media in the bloodstream of the patient which results in enhanced image quality.

Power injection procedures generate high pressures within the infusion system, thereby requiring specialized vascular access devices, extension sets, media transfer set, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant back pressure within the infusion system that commonly results in a failure of the infusion system components.

Traditionally, rapid infusion therapy entails the use of an intravenous catheter attached to a peristaltic pump and a fluid source. A patient is infused as a tip portion of the catheter is inserted into the vasculature of a patient and the pump forces a fluid through the catheter and into the patient's vein. Current rapid infusion therapies utilize a catheter and catheter tip with geometries identical to those used with traditional, routine infusion rates. These geometries include a tapering catheter tip such that the fluid is accelerated as the fluid moves through the catheter tip and exits into a patient's vasculature. This acceleration of the infused fluid is undesirable for several reasons.

For example, the tapered catheter results in a greater backpressure for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, the fluid acceleration in the catheter tip results in a recoil force that may cause the catheter tip to shift within the patient's vein thereby displacing the catheter and/or damaging the patient's vein and/or injection site. Fluid acceleration also increases the jet velocity of the infusant at the tip of the catheter. In some procedures, the fluid jet may pierce the patient's vein wall thereby leading to extravasation or infiltration. Not only is this uncomfortable and painful to the patient, but infiltration may also prevent the patient from receiving the needed therapy.

Accordingly, the problem of increased exit velocity of an infusant during rapid infusion procedures remains to be solved. Thus, the present disclosure presents systems and methods to reduce the exit velocity of an infusant while maintaining an increased rate of infusion, as is desirable during rapid infusion procedures.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient rapid infusion procedures.

One aspect of the present invention provides an improved vascular access device for use in combination with a vascular infusion system capable of rapidly delivering an infusant to the vascular system of a patient. The vascular access device generally includes an intravenous catheter configured to access the vascular system of a patient. The intravenous catheter is coupled to the vascular infusion system via a section of intravenous tubing. The material of the intravenous catheter may include a polymer or metallic material compatible with infusion procedures.

In some embodiments, a tip portion of the intravenous catheter is modified to include a plurality of diffusion holes. The tip portion generally comprises a tapered profile, wherein the outer and inner surface of the tip taper towards the distal end of the catheter. The tapered outer surface provides a smooth transition between the narrow diameter of the catheter tip opening and the larger diameter of the catheter tubing. Thus, as the tip of the catheter is introduced into the vein of a patient, the tapered outer surface facilitates easy insertion of the catheter through the access hole. The tapered inner surface is generally provided to tightly contact the outer surface of an introducer needle housed within the lumen of the catheter. The introducer needle is provided to create an opening into the vein of patient through which the catheter tip is inserted. The tapered inner surface ensures a tight seal between the inner surface of the catheter and the outer surface of the needle. Following placement of the catheter, the introducer needle is removed.

As an infusant passes through the tapered portion of the inner surface, the fluid flow of the infusant is accelerated due to the decreased volume through the tapered tip. Thus, in some embodiments a plurality of diffusion holes are formed through the wall thickness of the intravenous catheter so as to provide a plurality of pathways through the wall of the intravenous catheter. Thus, as infusant flows through the catheter toward the tip of the catheter, a portion of the bulk flow through the catheter is diverted through the diffusion holes rather than through the main opening of the catheter tip. As such, the pressure within the infusion system is reduced as compared to systems incorporating standard intravenous catheter. Additionally, the plurality of diffusion holes reduce the jet velocity issued from the tip of the catheter, thereby enabling increased flow rates as required by some diagnostic procedures without additional damage to the vein wall.

In some embodiments, the diffusions holes are arranged on the catheter tip in a staggered array such that an upstream diffusion hole is unaligned with a downstream hole. As such, the fluid flow of an infusant that issues from a downstream diffusion hole is not disturbed by the fluid flow of an infusant that issues from an upstream diffusion hole. This feature provides increased flow efficiency through downstream diffusion holes.

In some embodiments of the present invention, a first set of diffusion holes is disposed in a first annular ring at an upstream, axial position of the catheter tip. A second set of diffusion holes is further disposed in a second annular ring at an axial position of the catheter tip that is downstream from the first annular ring. In some embodiments, the holes of the first annular ring are staggered from the holes of the second annular ring so as to be generally unaligned. In other embodiments, the holes of the first annular ring are axially staggered from the holes of the second annular ring from about 15° to about 60°. Finally, in some embodiments the holes of the first annular ring are axially staggered from the holes of the second annular ring about 45°.

In some embodiments, the diffusion holes are provided through the catheter wall at a predetermined bore angle. Specifically, the diffusion holes of the present invention include an inner wall surface that may be angled relative to the inner surface of the catheter lumen. In some embodiments, the inner surface of a diffusion hole is oriented to an acute angle relative to the inner surface of the catheter lumen. In other embodiments, an inner surface of the diffusion hole is oriented to an angle from about 15° to about 75° relative to the inner surface of the catheter lumen. In some embodiments, the bore angle of the diffusion hole is selected so as to optimize flow efficiency through the diffusion hole, catheter tension within the vein, centralized positioning of the catheter tip within the vein, and reduction of system pressure and tip jet velocity within an infusion system.

The present invention further includes methods for manufacturing an intravenous catheter for diffusing an infusant. Some methods include the steps of providing an intravenous catheter and forming a plurality of staggered holes through the wall thickness of the intravenous catheter. Some methods of the present invention further include using a laser drill to provide the various staggered holes.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
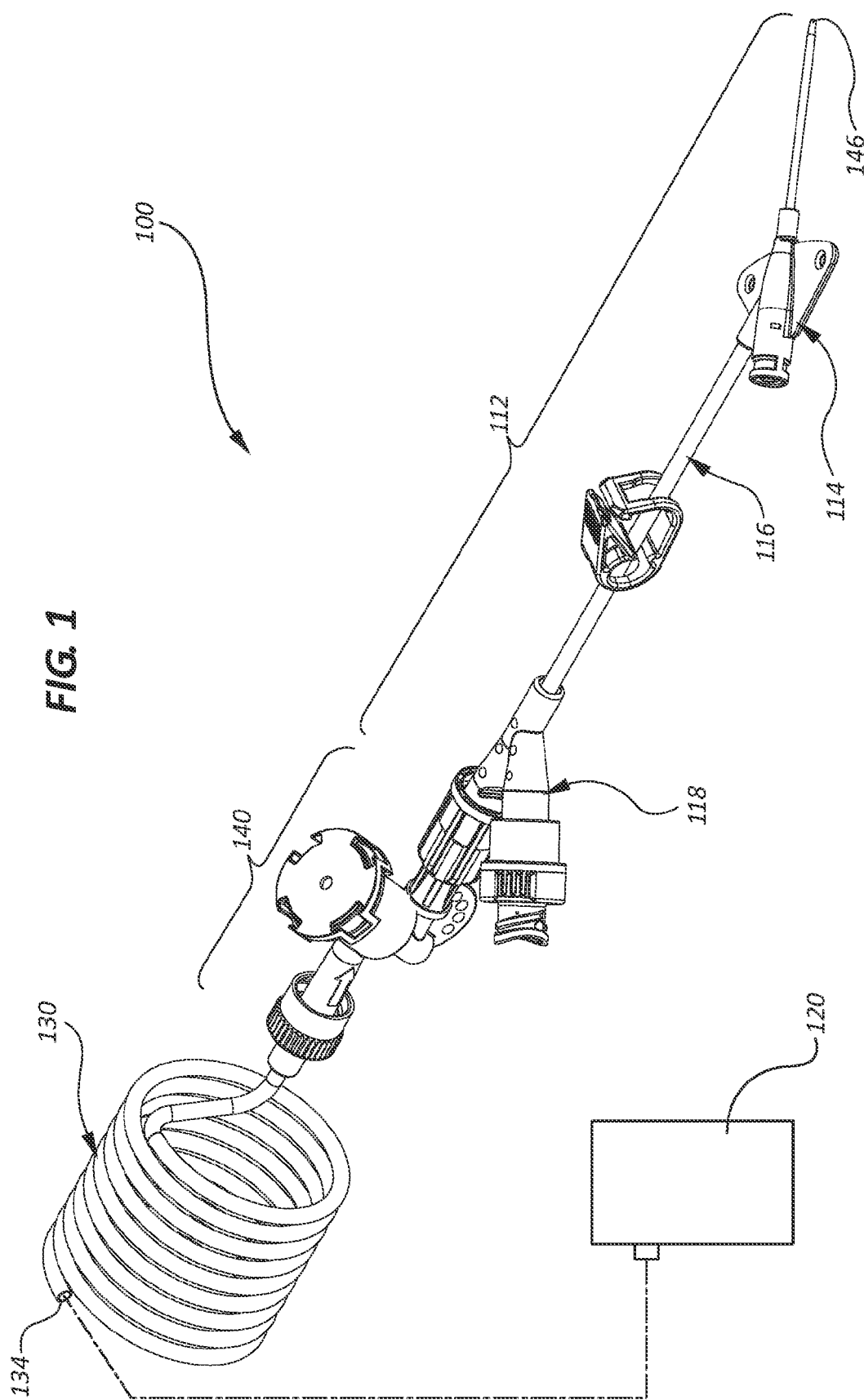
FIG. 1 is a perspective view of an infusion system in accordance with a representative embodiment of the present invention.

The systems and methods of the present invention are generally designed for use in combination with a vascular infusion system capable of rapidly delivering an infusant to the vascular system of a patient. Referring now to FIG. 1, a vascular infusion system 100 is shown, in accordance with a representative embodiment of the present invention. Infusion systems of this type are commonly configured to operate at internal pressures up to 2000 psi. Many systems operate in the range of 75 to 2000 psi, while specific devices of this type operate at 100, 200, and 300 psi. The vascular infusion system 100 comprises a vascular access device 112 coupled to an injector pump 120 via a coiled extension set 130. In some embodiments, the infusion system 100 further comprises a safety device 140 positioned between the vascular access device 112 and the injector pump 120. In some embodiments, a safety device 140 is provided to automatically occlude the fluid path of the infusion system 100, thereby preventing excessive pressure buildup in downstream infusion components.

An injector pump 120 generally comprises a fluid pumping apparatus configured to rapidly deliver an infusant, such as blood, medicaments, and CT scan contrast agents to a patient's vascular system. Desirable infusants may also include various fluids often of high viscosity as required for medical and diagnostic procedures. In some embodiments, the injector pump 120 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 120 and a vascular access device 112 are selected to compatibly achieve a desired infusion flow rate.

A coiled extension set 130 generally comprises flexible or semi-flexible polymer tubing configured to deliver an infusant from the injector pump 120 to the vascular access device 112. The extension set 130 includes a first coupler 132 for connecting the extension set 130 to a downstream device 112 or 140. The extension set 130 also includes a second coupler 134 for connecting the extension set 130 to the injector pump 120. A coiled configuration of the extension set 130 generally prevents undesirable kinking or occlusion of the set 130 during infusion procedures. However, one of skill in the art will appreciate that the extension set 130 may include any configuration capable of efficiently delivering an infusant from an injector pump 120 to the patient via a vascular access device 112. In some embodiments, the extension set 130 is coupled between a syringe and a vascular access device whereby an infusant is manually injected into a patient. In other embodiments, the infusion system comprises only a syringe and a vascular access device, in accordance with the present invention.

The vascular access device 112 generally comprises a peripheral intravenous catheter 114. A peripheral intravenous catheter 114 in accordance with the present invention generally comprises a short or truncated catheter (usually 13 mm to 52 mm) that is inserted into a small peripheral vein. Peripheral intravenous catheters 114 are typically designed for temporary placement. The short length of the catheter 114 facilitates convenient placement of the catheter but makes them prone to premature dislodging from the vein due to movement of the patient and/or recoil forces experienced during infusion procedures. Furthermore, unlike midline or central peripheral catheters, peripheral intravenous catheters 114 in accordance with the present invention comprise a tapered catheter tip 146 to accommodate use with an introducer needle (not shown) designed to aid in insertion of the catheter 114.

An introducer needle is typically inserted through the catheter 114 such that a tip of the needle extends beyond the tapered tip 146. The tapered geometry of the tapered tip 146 conforms tightly to the outer surface of the introducer needle. Both the outer surface and the inner surface of the tip 146 are tapered towards the distal end of the catheter 114. The outer surface of the tip 146 is tapered to provide a smooth transition from the smaller profile of the introducer needle to the larger profile of the catheter outer diameter. Insertion of the introducer needle into the vein of the patient provides an opening into the vein through which the tapered tip 146 of the catheter 114 is inserted. The tapered outer surface of the tip 146 enables easy insertion of the catheter 114 into the opening. Once the peripheral intravenous catheter 114 is inserted into the vein of the patient, the introducer needle (not shown) is removed from the lumen of the catheter 114 to permit infusion via the catheter 114.

The tapered inner surface of the tip 146 provides a secure seal between the inner surface of the catheter tip 146 and the outer surface of the introducer needle (not shown). Additionally, the tapered inner surface of the tip 146 causes an acceleration of infusant within the lumen of the catheter as the infusant nears and flows through the catheter tip 146. Specifics regarding the geometries of the tapered inner surface of the tip 146 are provided in connection with FIGS. 3B and 4B below. Following an infusion procedure, the peripheral intravenous catheter 114 is simply removed from vein and discarded.

A desired infusant is typically delivered to the catheter 114 via a section of intravenous tubing 116 coupled to the catheter 114. In some embodiments, a y-adapter 118 is coupled to an end of the tubing 116 opposite the catheter 114, enabling the vascular access device 112 to be coupled to the remainder of the vascular infusion system 100. One of skill in the art will appreciate the possible variations and specific features of available vascular access devices 112, as are commonly used in the medical and research professions. For example, in some embodiments a catheter 114 in accordance with the present invention may include additional access sites, clamps, parallel intravenous lines, valves, couplers, introducer needles, coatings, and/or materials as desired to fit a specific application.

Figure 2:
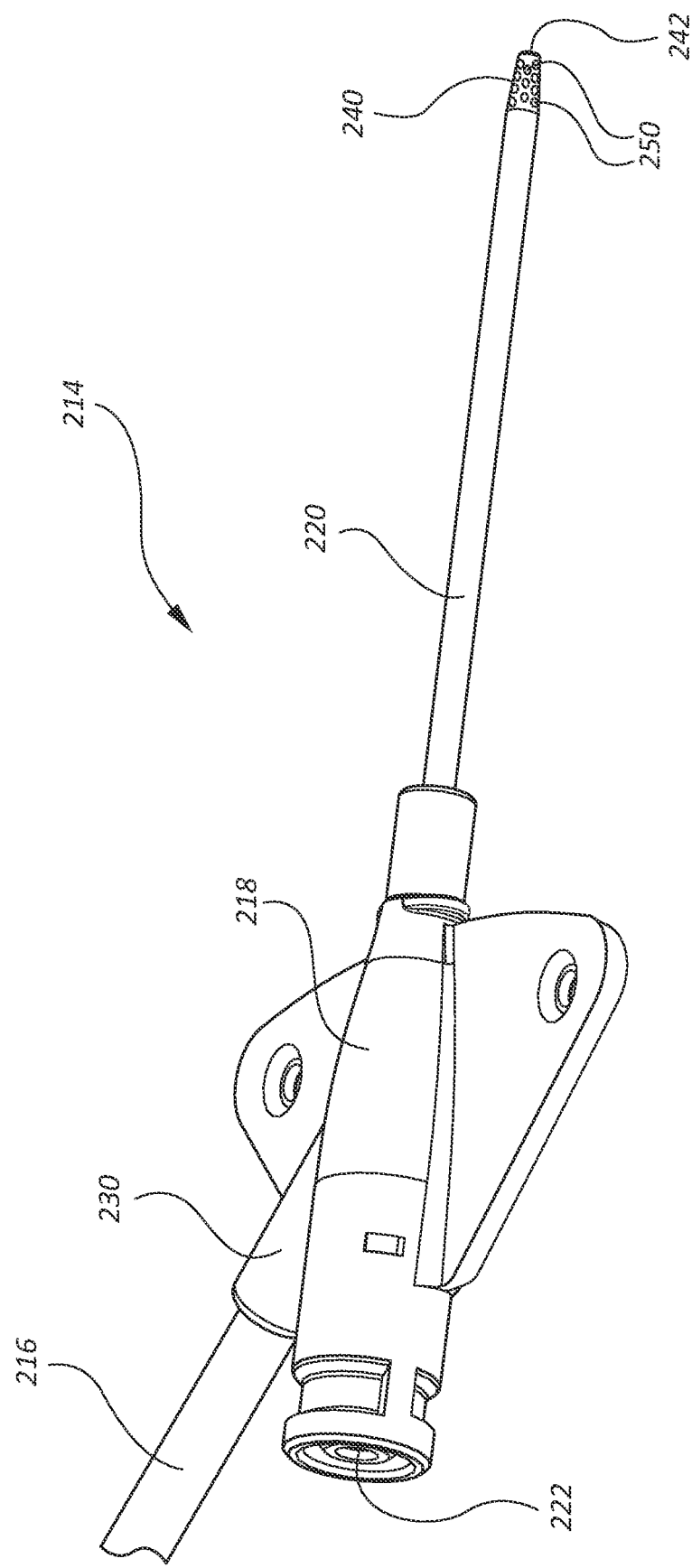
FIG. 2 is a detailed perspective view of a catheter in accordance with a representative embodiment of the present invention.

Referring now to FIG. 2, a catheter 214 is shown in accordance with a representative embodiment of the present invention. Catheter 214 generally comprises a catheter adapter 218 configured to house a tubular body member 220. Catheter adapter 218 further includes an inlet port 230 that is coupled to a section of intravenous tubing 216. The section of intravenous tubing 216 is further coupled to upstream infusion components, as shown and described in connection with FIG. 1, above.

The catheter adapter 218 facilitates delivery of an infusant within the intravenous tubing 216 to a patient via the tubular body member 220. An inner lumen of the catheter adapter 218 is in fluid communication with both an inner lumen of the intravenous tubing 216 and an inner lumen of the tubular body member 220. In some embodiments, catheter adapter 218 further comprises an access port 222. The access port 222 is generally provided to permit direct access to the inner lumen of the catheter adapter 218. In some embodiments, the access port 222 is accessed via a needle and a syringe to deliver an infusant to a patient via the tubular body member 220. In other embodiments, an introducer needle or guide wire is inserted into the access port 222 and advanced through the inner lumen of the tubular body member 220. In some embodiments, a tip portion of the introducer needle or guide wire (not shown) extends beyond a tip portion 240 of the tubular body member 220. As such, the tip portion of the introducer needle or guide wire may provide an opening into the vascular system of a patient into which the tubular body member 220 is inserted. Following placement of the tubular body member 220 into the vein of the patient, the introducer needle or guide wire is removed from the access port 222 thereby establishing fluid communication between the tubular body member 220, the catheter adapter 218 and the intravenous tubing 216.

In some embodiments, the tubular body member 220 comprises an intravenous catheter. The intravenous catheter 220 generally comprises a flexible or semi-flexible biocompatible material, as commonly used in the art. In some embodiments, the intravenous catheter 220 comprises a polymer material, such as polypropylene, polystyrene, polyvinylchloride, polytetrafluoroethylene, and the like. In other embodiments, the intravenous catheter 220 comprises a metallic material, such as surgical steel, titanium, cobalt steel, and the like.

The tubular body member 220 may comprise any length, where the length is selected based on the intended application of the catheter 214. For some applications, the tubular body member 220 is inserted into a peripheral vein of the patient. In other applications, the tubular body member 220 is inserted into a central vein of the patient. For rapid infusion applications, the tip portion 240 of the tubular body member 220 is modified to include a plurality of diffusion holes 250. The diffusion holes 250 are generally provided to divert fluid from the main channel of flow through the inner lumen of the tubular body member 220. As such, the diffusion holes 250 effectually slow the jet of infusant which issues from the catheter tip 240 during rapid infusion procedures. Additionally, the plurality of diffusion holes 250 increase the accumulative area of the catheter tip opening 242 to relieve the overall pressure in the vascular infusion system 100.

Figure 3A:
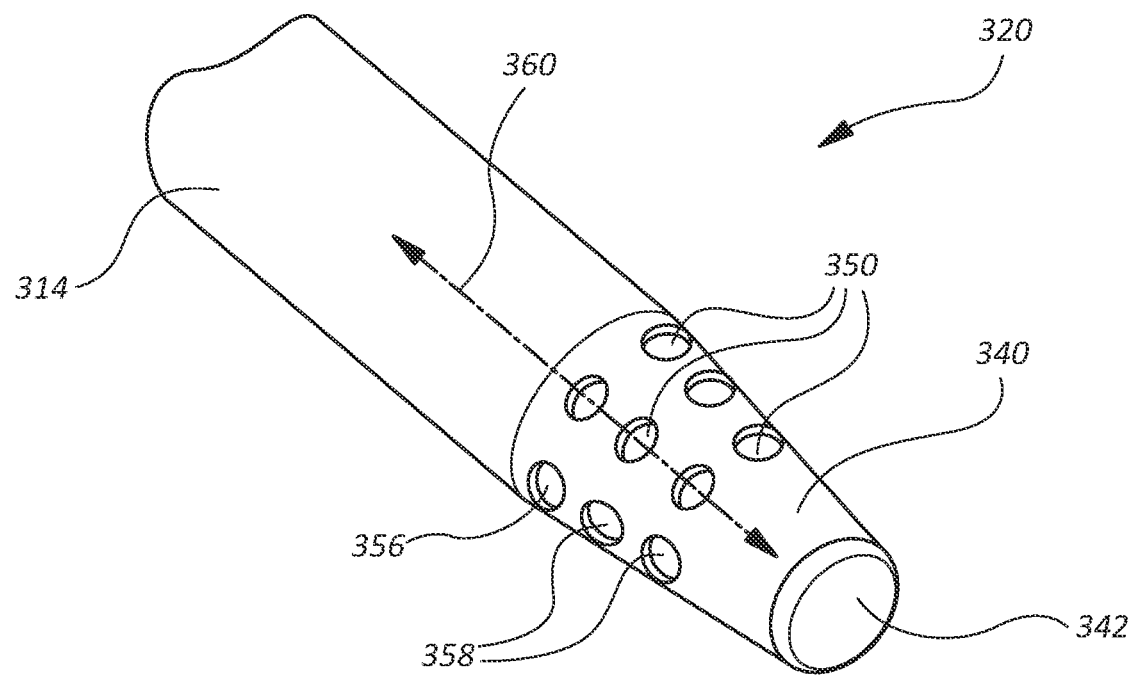
FIG. 3A is a perspective view of a catheter tip in accordance with a representative embodiment of the present invention.

Referring now to FIG. 3A, a distal end portion 320 of an intravenous catheter 314 is shown, in accordance with a representative embodiment of the present invention. As previously discussed, an external surface of the tip 340 is tapered so as to provide a gradual transition from the catheter opening 342 of the tip 340 to the diameter of the catheter body 314. In some embodiments, the tip 340 of the intravenous catheter 314 is modified to include a plurality of side holes 350. The side holes 350 are generally positioned on the tapered tip 340 of the catheter 314 to provide an access through which infusant within the catheter 314 may issue. The surface area of the side holes 350 combine with the surface area of the lumen opening 342 to increase the overall surface area through which an infusant may issue from the tip 340 of the intravenous catheter 314. The side holes 350 are annularly organized on the tip 340 of the intravenous catheter 314 so as to align adjacent holes along a common axis 360. As such, an upstream hole 356 is directly aligned with downstream holes 358.

Figure 3B:
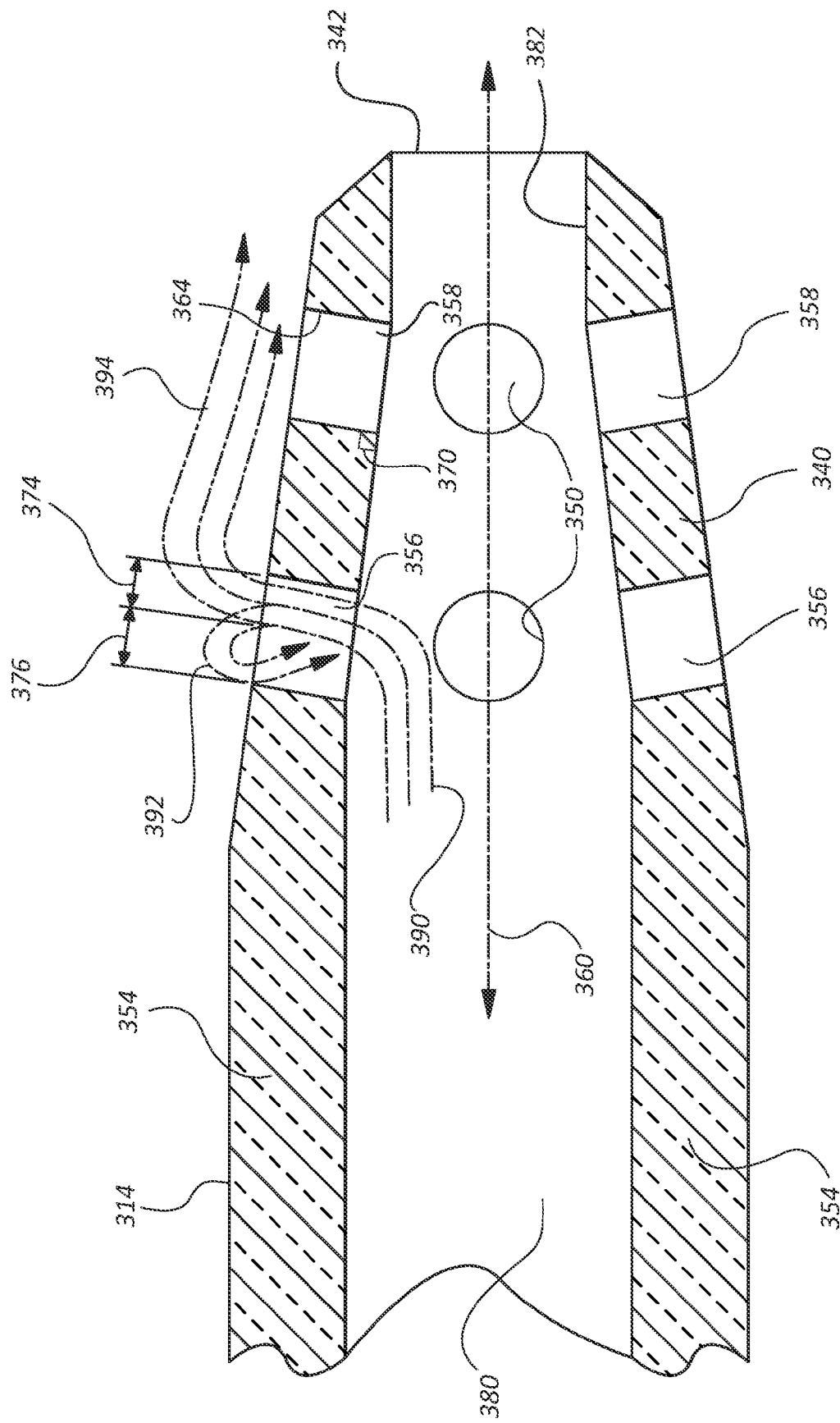
FIG. 3B is a cross-section side view of the catheter tip of FIG. 3A in accordance with a representative embodiment of the present invention.

Referring now to FIG. 3B, a cross-sectioned view of the intravenous catheter 314 of FIG. 3A is shown. As previously discussed, a portion 334 of the internal surface of the tip 340 is tapered which causes an acceleration in the fluid flow 390 through the tip 340. The side holes 350 of the intravenous catheter 314 are formed through the catheter wall 354 such that an inner surface 364 of each hole 350 is oriented at an angle 370 of approximately 90° relative to an inner surface 382 of the catheter lumen 380. The side holes 350 are generally positioned within the tapered portion 334 of the tip 340 such that as the velocity of the fluid flow 390 increases through the tapered portion 334, infusant 394 is permitted to issue through the side holes 350. As infusant issues through the side holes 350, fluid pressure within the lumen 380 is decreased. Additionally, as infusant issues through the side holes 350, tip jet velocity of the infusant also decreases.

Computational fluid dynamic analysis of the 90° side holes 350 reveals that only a first half 374 of each hole 350 cross section is utilized by the fluid flow 390. In some embodiments, a second half 376 of the 90° side holes 350 cross section comprises a recirculation eddy 392. Therefore, in some embodiments the 90° side hole 350 configuration may demonstrate approximately fifty percent flow efficiency through each side hole 350.

Figure 4A:
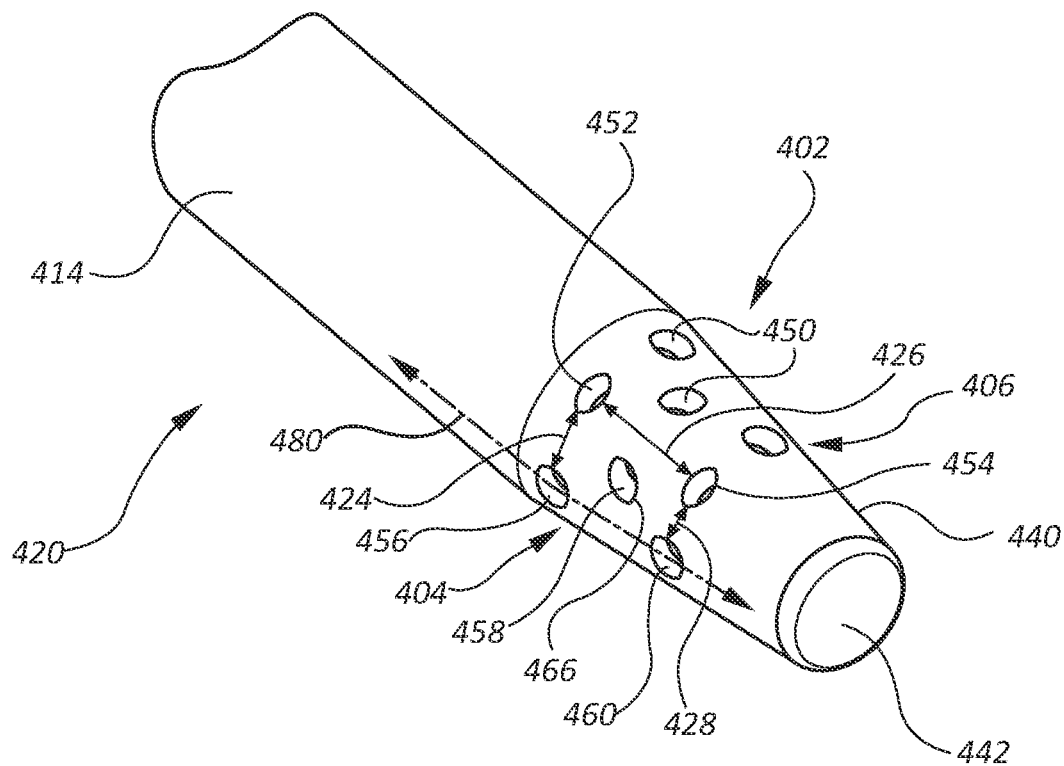
FIG. 4A is a perspective view of a catheter tip in accordance with a representative embodiment of the present invention.

Referring now to FIG. 4A, a distal end portion 420 of an intravenous catheter 414 is shown in accordance with a representative embodiment of the present invention. The intravenous catheter 414 has been modified to include a plurality of staggered diffusion holes 450. One having skill in the art will appreciate that the number and dimensions of the diffusion holes 350 and 450 may be varied and adjusted to achieve a desired flow rate, a reduction in tip jet velocity, a reduction in vascular damage, and increased bolus density. Diffusion holes 350 and 450 are generally provided by manufacturing methods known in the art. For example, in some embodiments the plurality of diffusion holes 350 and 450 are provided with a laser drill.

In some embodiments, a selected array of the diffusion holes 450 increases the distance between adjacent holes 450 thereby structurally strengthening the tip 440 of the intravenous catheter 414, as compared to some linear hole arrays. In other embodiments, a selected array of the diffusion holes 450 further streamlines infusant issued from the diffusion holes 450 thereby reducing the energy necessary to divert bulk flow from the main stream of the catheter lumen 490 into the diffusion holes 450.

For example, in some embodiments of the present invention the diffusion holes 450 have been arranged in a staggered configuration, as shown. Accordingly, an upstream hole 456 is unaligned with an adjacent, downstream hole 458. Furthermore, downstream hole 458 is unaligned with an adjacent, downstream hole 460. In some embodiments, upstream hole 456 is directly aligned with downstream hole 460 along a common axis 480. In other embodiments, upstream hole 456, downstream hole 458 and downstream hole 460 are each unaligned with each other, such that none of the holes are aligned along a common axis. In some embodiments, an upstream hole 456 is axially staggered from a downstream hole 458 from about 15° to about 60°. Finally, in some embodiments, an upstream hole 456 is axially staggered from a downstream hole 458 approximately 45°.

The diffusion holes 450 are annularly organized on the tapered portion of the tip 440 of the intravenous catheter 414 in a staggered configuration, as previously discussed. A first annular ring 402 comprises a plurality of diffusion holes 450 forming a first upstream ring of diffusion holes. In some embodiments, the holes of the first annular ring 402 are axially spaced an equal distance from adjacent holes of the first annular ring 402. In other embodiments, a non-uniform axially spacing is applied to the holes of the first annular ring 402. In some embodiments, a second annular ring 404 is provided downstream from the first annular ring 402, the diffusion holes of the second annular ring 404 being staggeredly positioned relative to the diffusion holes of the first annular ring 402. Finally, in some embodiments a third annular ring 406 is provided downstream from the second annular ring 404, the diffusion holes of the third annular ring 406 being staggeredly positioned relative to the diffusion holes of the second annular ring 404.

A gap 424 is provided between adjacent holes of the first annular ring 402. In some embodiments, the gap 424 is provided to accommodate the width of downstream hole 458, such that the downstream hole 458 and the gap 424 are aligned along a common axis (not shown). Furthermore, a downstream gap 428 is provided to accommodate the width of an upstream hole 466, such that the upstream hole 466 and the downstream gap 428 are aligned along a common axis (not shown). The axial alignment of the upstream gap 424 and the downstream hole 458 prevents wake effect due to the absence of a diffusion hole directly upstream from the downstream hole 458. Similarly, the axial alignment of the downstream gap 428 and the upstream hole 466 prevents wake effect due to the absence of a diffusion hole directly downstream from the upstream hole 466.

The staggered configuration of the first, second and third annular rings 402, 404 and 406 provides an elongate gap 426 forming a space between an upstream diffusion hole 452 of the first annular ring and an axially aligned downstream diffusion hole 454 of the third annular ring 406. The length of the elongate gap 426 generally provides sufficient distance between an upstream diffusion hole 452 and a downstream diffusion hole 454, so that the fluid pressure of an infusant from the upstream hole 452 is approximately equal to the fluid pressure of an infusant from the downstream hole 454. Thus, the staggered configuration of the diffusion holes 450 ensures equal flow efficiency from upstream and downstream diffusion holes 452 and 454.

Figure 4B:
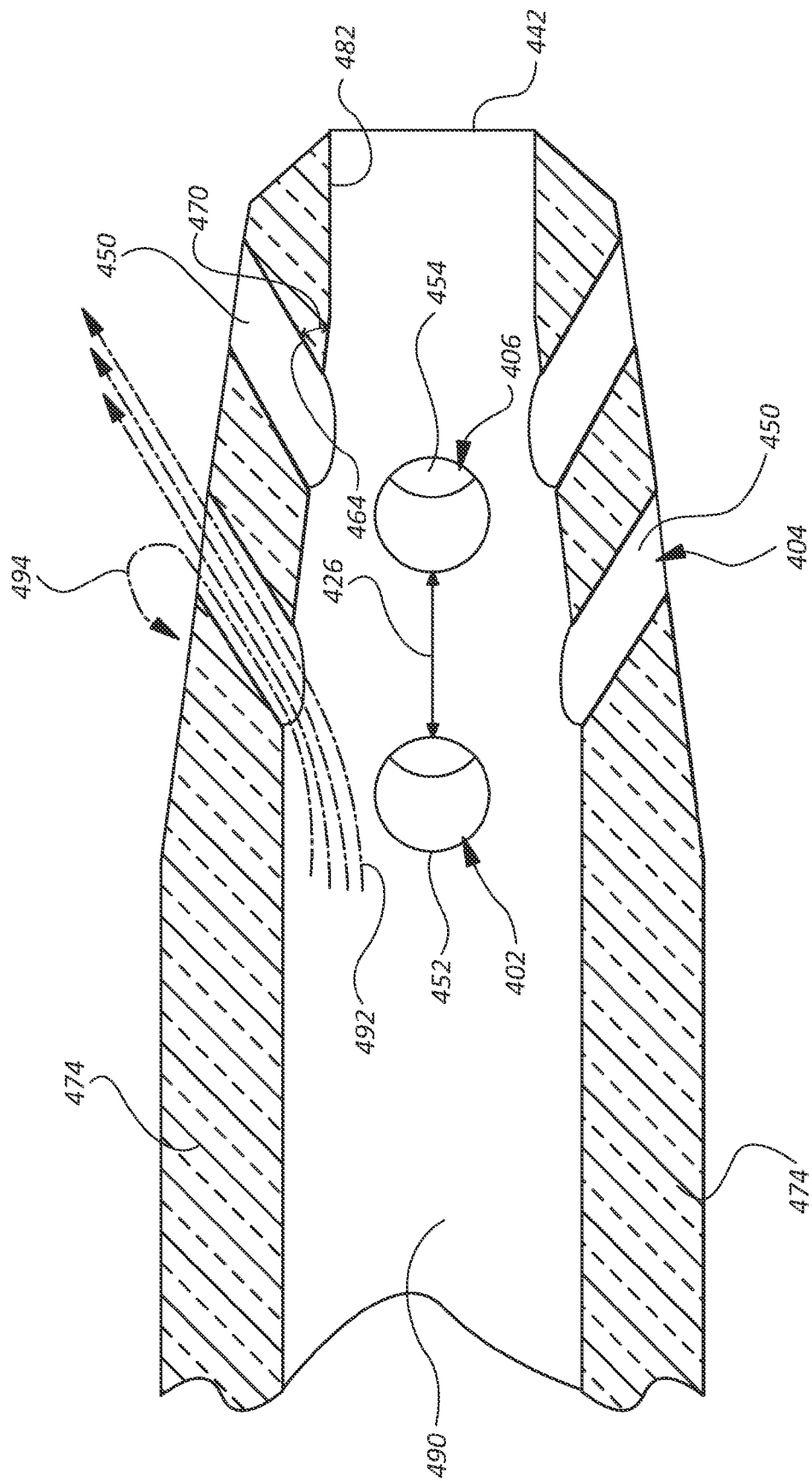
FIG. 4B is a cross-section side view of a catheter tip in accordance with a representative embodiment of the present invention.

In some embodiments, the diffusion holes 450 are formed through the catheter wall 474 such that an inner surface 464 of each hole 450 is oriented at an angle 470 that is acute to an inner, tapered surface 482 of the catheter lumen 490, as shown in FIG. 4B. In some embodiments, the angle 470 is between about 15° to about 75°. In other embodiments, the angle 470 is approximately 45°.

EXAMPLES

To decrease the amount of contrast media required for a diagnosis, the concentration of contrast media per unit volume of blood needs to be increased by increasing the volumetric flow rate of the of contrast media without increasing the catheter tip velocity. The elements of the present invention achieve these required objectives, as demonstrated in the examples below.

Example 1

Tip Jet Velocity Comparison

The jet velocities at the tip of a standard catheter are in excess of 1,000 in/sec for a 5 ml/sec volumetric flow rate setting, which results in a large force applied to the vein wall of a patient. This force is treacherous for patients with non-optimal vein structure provisions increasing the likelihood of extravasation or intima damage with increasing flow rates.

Figure 5:
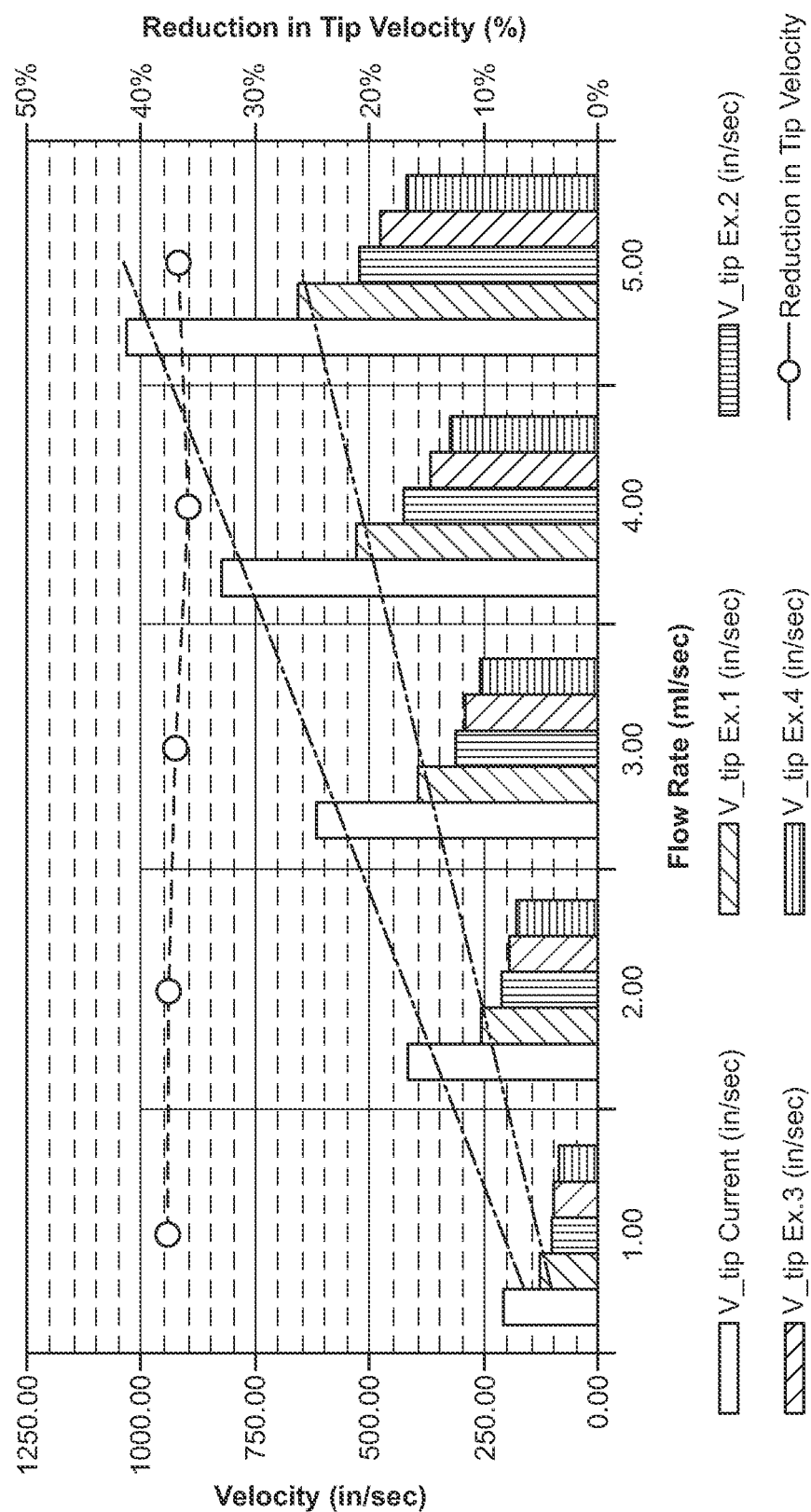
FIG. 5 is a graphical representation of jet tip velocities at various flow rates in accordance with representative embodiments of the present invention.

Jet tip velocities of a standard 22 GA×1.00" catheter (V_tip Current) were compared to a 22 GA×1.00" catheter (V_tip Ex. 1-V_tip Ex. 4) modified to include a plurality of diffusion holes, as described in connection with FIGS. 4A and 4B, above. Quadruplicate samples of the modified catheter were tested at flow rates of 1 ml/sec, 2 ml/sec, 3 ml/sec, 4 ml/sec, and 5 ml/sec. Tip jet velocity was then recorded for each sample and compared to the jet velocity of the standard catheter at each flow rate. The experiment demonstrated that the overall tip jet velocity of the modified catheter was decreased by 36% over the standard catheter. The results of the experiment are shown in FIG. 5.

Example 2

System Pressure Comparison

Internal pressures within an infusion system were compared between an infusion system using a standard 22 GA×1.00" catheter and an infusion system using a 22 GA×1.00" catheter (P_inj #1 and P_inj #2) modified to include a plurality of diffusion holes, as described in connection with FIGS. 4A and 4B, above.

Figure 6:
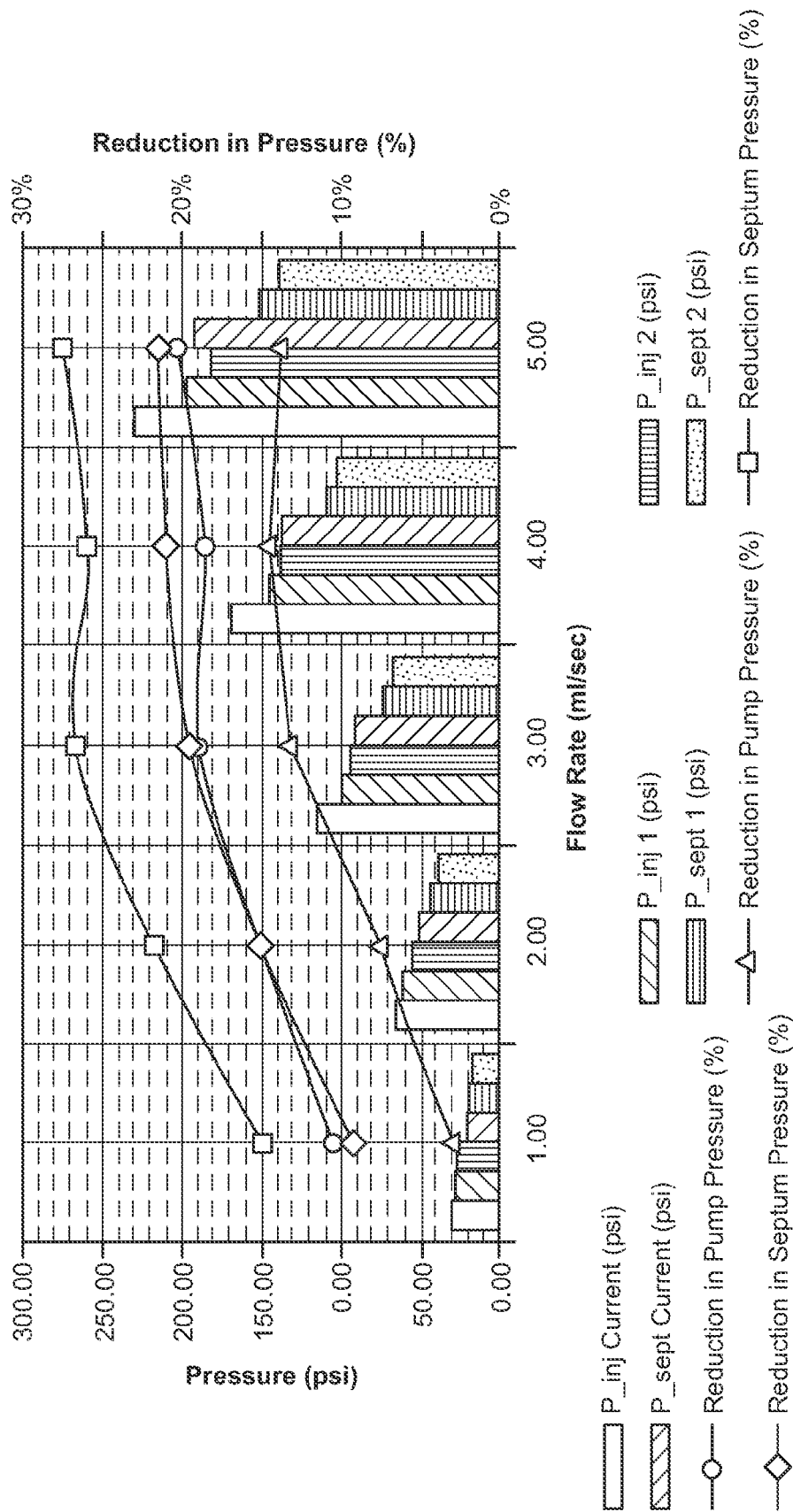
FIG. 6 is a graphical representation of system pressures at various flow rates in accordance with representative embodiments of the present invention.

System pressure was measured both within each infusion pump (P_inj Current, P_inj 1 and P_inj 2) and the inner lumen of each catheter (P_sept Current, P_sept 1 and P_sept 2). System pressure was tested and recorded at flow rates of 1 ml/sec, 2 ml/sec, 3 ml/sec, 4 ml/sec, and 5 ml/sec. System pressures at each flow rate where then graphed, as shown in FIG. 6.

The results of the experiment demonstrate an increase in the volumetric flow rate by decreasing system pressure by nearly 30%, with the greatest reduction in pressure being shown within the lumen of the modified catheters.

Example 3

Computational Fluid Dynamic Analysis

Computation fluid dynamic analysis was conducted on a standard 22 GA×1.00" catheter modified to include a plurality of diffusion holes bored approximately 45° relative to the inner wall surface of the catheter. The analysis revealed an addition 6% diversion of bulk flow from the main stream into the diffusion holes, as compared to a standard 22 GA×1.00" catheter having a plurality of diffusion holes bored 90° relative to the inner wall surface of the catheter. The analysis further revealed a significant increase in fluid flow 492 through the cross section of the diffusion hole 450, as compared to the straight holes of the standard catheter. While the diffusion holes 450 of the present invention did show a slight recirculation eddy 494, the recirculation eddy 494 was significantly weaker as compared to the circulation eddy 392 of the standard catheter. A representative rendering of the fluid flow 492 is shown in FIG. 4B.

Example 5

Catheter Stabilization and Vein Centering

In standard peripheral intravenous catheters, the inner lumen of the catheter tapers towards the tip of the catheter resulting in a recoil force as an infusant accelerates through the constriction. This force is akin to the force felt when holding a fire hose. Like a fire hose, a catheter tip under the compressive recoil force is unstable and can oscillate violently within the vein (also known as catheter whip) causing vein damage, as previously discussed. If enough infusant is turned from the axial direction through diffusion holes, then the recoil force will become negative and actually pull the catheter tip into tension; the tensioned state of the catheter tip providing great stability to the inserted catheter. Therefore, in some embodiments the bore angle is strategically selected to balance between increased flow through the diffusion holes and decreased recoil force on the catheter tip by reducing the axial direction of infusant flowing through the diffusion holes.

The bore angle further affects the positioning of the catheter within the vein. For example, when inserted in to a vein the venous catheter generally extends through the skin and into the vein at approximately 30°. As such, the tip of the venous catheter commonly contacts or rests against the inner wall of the vein opposite the insertion site of the catheter. As fluid flow increases, high jet velocity from the catheter tip is exerted directly on the inner wall of the vein. However, when the tip of the venous catheter is modified to include diffusion ports, the diverted infusant that issues from the diffusion ports pushes the catheter tip away from the vein wall resulting in a centralized position of the catheter tip within the vein. Thus, the jet velocity from the tip is directed into the fluid stream of the vein rather than into the vein wall.

Figure 7A:
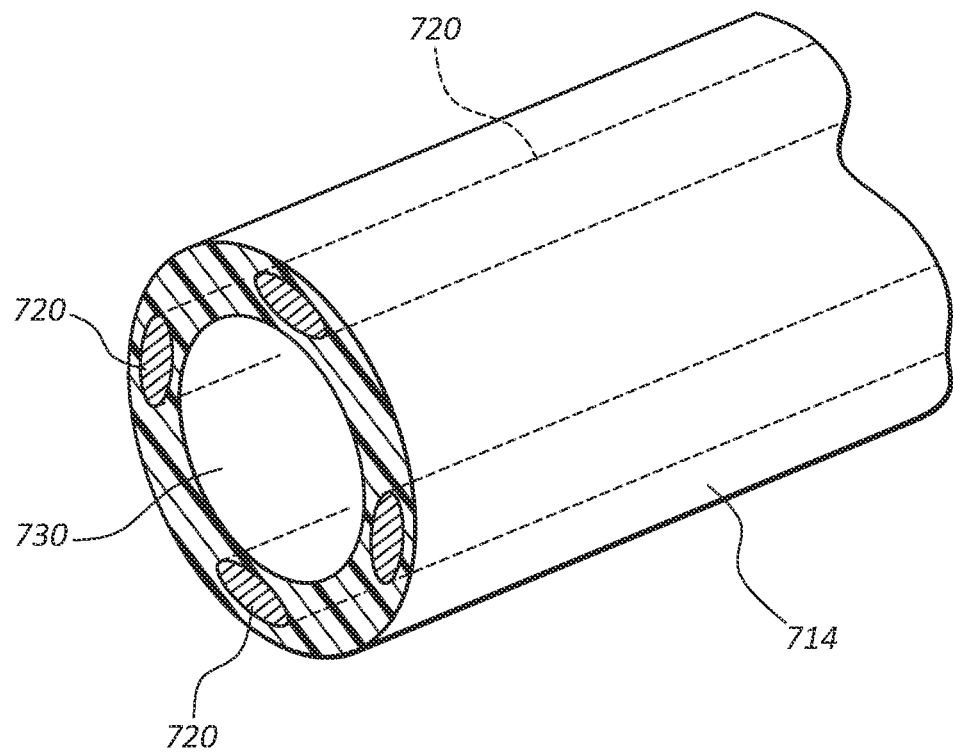
FIG. 7, shown in parts A and B, illustrates a catheter tube body having an extruded stripe material in accordance with a representative embodiment of the present invention.

In some embodiments, a method is provided for manufacturing a peripheral catheter having a plurality of diffusion holes. Some methods provide steps whereby an extruded catheter tube body 714 is first cut to a desired length, as described above and as shown in FIG. 7.

Catheter tube body 714 comprises a continuous extrusion that is subsequently cut to a final length as determined by the type of application for which the catheter tube body 714 will be used. Plastic tubing, such as catheter tube body 714, is manufactured by extruding molten polymer through a die of the desired profile shape. For example, a die may be used to produce various shapes such as a square, a circle, a rectangle, or a triangle. Hollow sections are usually extruded by placing a pin or mandrel inside of the die and in most cases positive pressure is applied to the internal cavities through the pin.

In some embodiments, a process of coextrusion is utilized to provide extruded stripe material 720. Coextrusion refers to the extrusion of multiple layers of material simultaneously. This type of extrusion utilizes two or more extruders to melt and deliver a steady volumetric throughput of different molten plastics to a single extrusion head which combines the materials in the desired shape. The layer thicknesses are controlled by the relative speeds and sizes of the individual extruders delivering the materials.

Catheter tube body 714 may be produced by coextrusion wherein an inner and outer layer of clear, molten polymer material is extruded through an inner and outer extruder to a single, round extrusion head. A pin may also be centered inside the inner extruder to provide a lumen 730 for the catheter tube body 714. A middle extruder may also be positioned between the inner and outer extruders whereby a molten, stiffening material may be extruded and embedded between the inner and outer layers to provide stripe material 720. In some embodiments, stripe material 720 comprises a radiopaque material. In other embodiments, stripe material 720 comprises a material having greater density than the remaining material of catheter tube body 714.

Figure 7B:
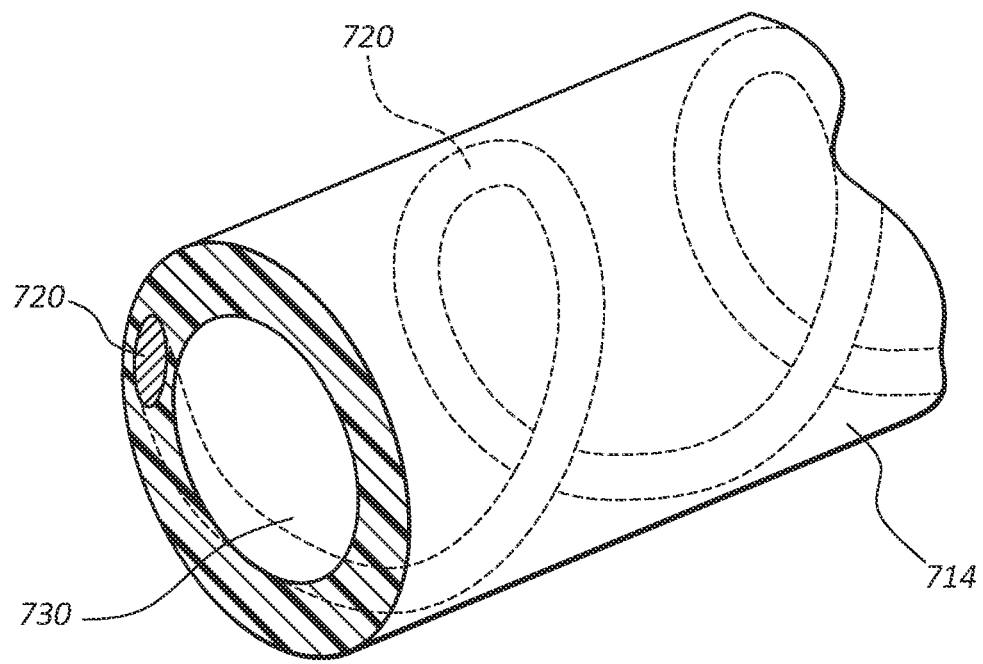

In some embodiments, a rotational position of the middle extruder is fixed, thereby providing linearly configured extruded stripe material 720. In other embodiments, the middle extruder is rotatably positioned between the inner and outer extruders. As such, the middle extruder may rotate independent of the inner and outer extruders thereby permitting stripe material 720 to be embedded between the inner and outer layers in non-linear configurations, such as a helical configuration, as shown in FIG. 7B. Additional configurations and methods of extruding stripe material 720 are taught in U.S. patent application Ser. No. 12/120,436, which is incorporated herein by reference.

Figure 8A:
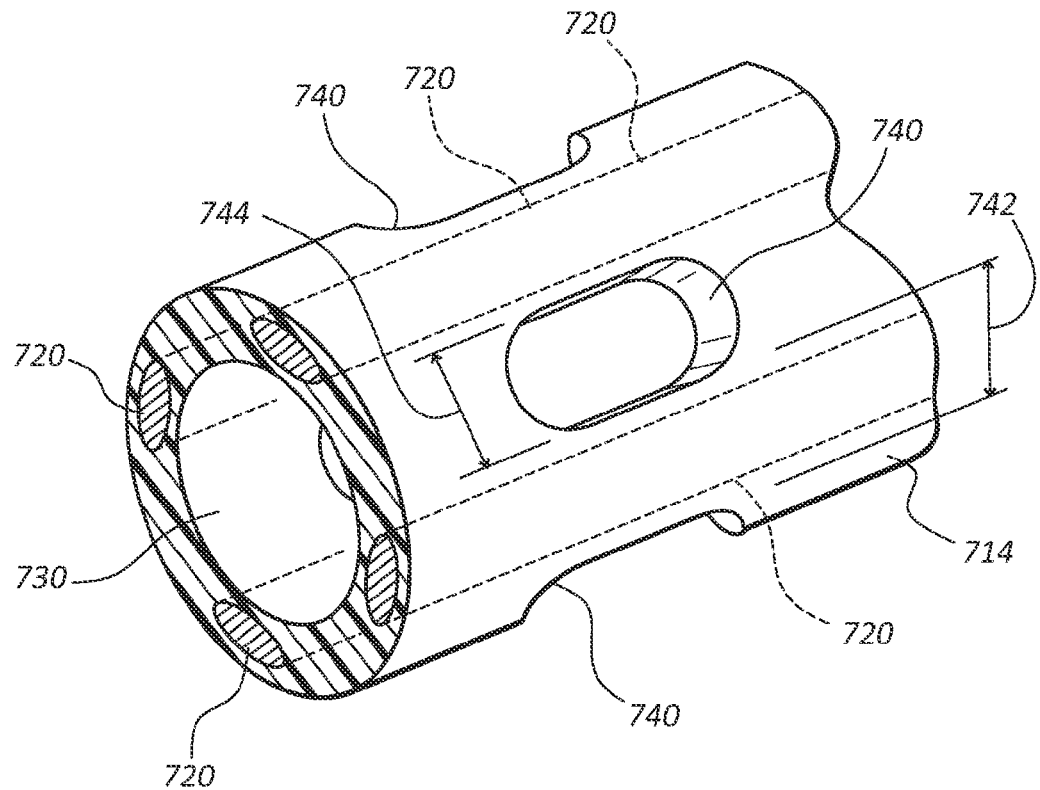
FIG. 8, shown in parts A and B, illustrates a catheter tube body having a plurality of diffusion holes in accordance with a representative embodiment of the present invention.
Figure 8B:
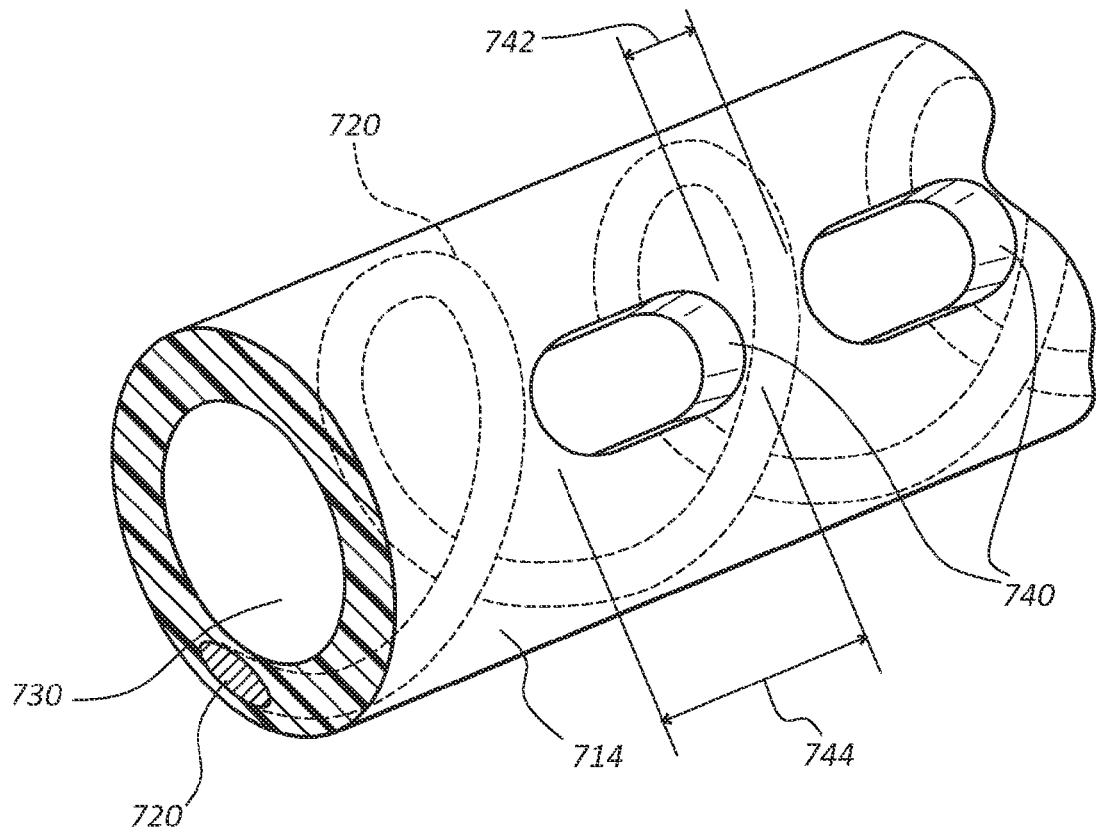

Once catheter tube body 714 has been cut to a desired length, one or more diffusion holes 740 are provided through the sidewall of catheter tube body 714, as shown in FIGS. 8A and 8B. Diffusion holes 740 may include any size, shape, configuration, geometry, orientation and number as may be desired. Examples of various diffusion hole configurations and geometries are taught herein and in U.S. patent application Ser. No. 12/853,804, which is incorporated herein by reference.

In some embodiments, the addition of diffusion holes 740 may weaken the structural integrity of catheter tube body 714. In particular, where multiple diffusion holes 740 are provided, the section of tubing material 742 interposed between two adjacent diffusion holes 740 is structurally weakened and prone to kinking or crushing during catheterization. Accordingly, in some embodiments stiffening material 720 is positioned between adjacent diffusion holes 740, or diffusion holes 740 are positioned between opposing surfaces of adjacent strands of stiffening material 720, as shown in FIG. 8A. As such, stiffening material 720 provides structural support and axial rigidity to the weakened sections of tubing material 742. Further, in some embodiments the interposed position of diffusion holes 740 promotes a catheter tip slitting failure rather than a catheter tip blow off failure mode, in the event of a catastrophic pressure spike situation. This is due to the likelihood of any yielding or failure to propagate from the distal diffusion hole along the length of the catheter to the tip, rather than causing the catheter tip to separate from body of the catheter.

In some embodiments, stiffening material 720 comprises two or more independent strands. In other embodiments, stiffening material 720 comprises a single strand, wherein the configuration of the single strand provides an unobstructed section of tubing 744 interposed between two adjacent surfaces of stiffening material 720 wherein diffusion hole 740 is positioned, as shown in FIG. 8B.

Figure 9:
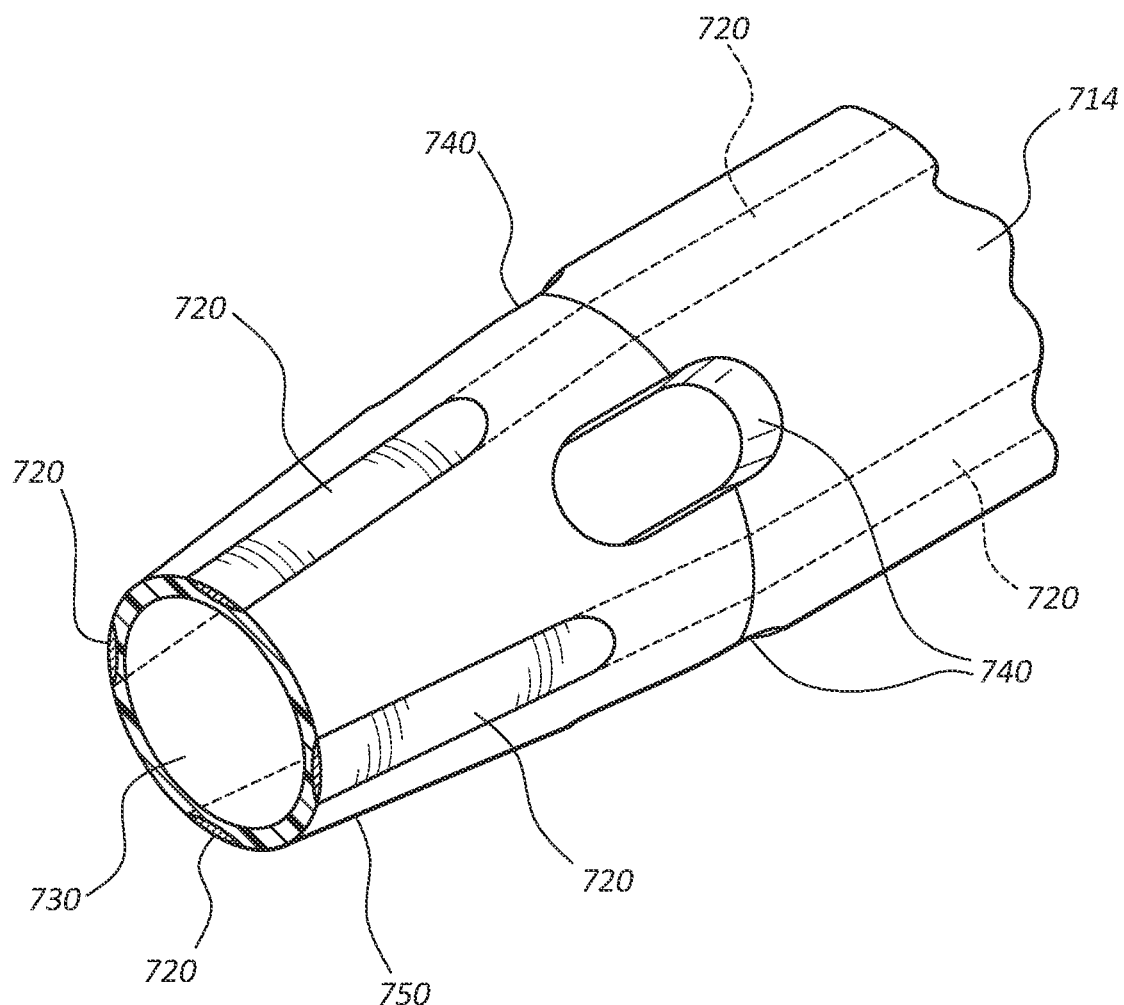
FIG. 9 illustrates a catheter tube body following a tipping procedure in accordance with a representative embodiment of the present invention.

Once diffusion holes 740 have been provided, catheter tube body 714 undergoes a tipping process, wherein a distal end of catheter tube body 714 is tapered, as shown in FIG. 9. The tipping process may be accomplished by any known methods in the art. Once tipped, the entire catheter tube body 714 is lubricated. In some embodiments, the order of steps wherein the diffusion holes 740 are provided prior to tipping the catheter tube body 714 eliminates any impact to the catheter tip 750 which may occur by drilling diffusion holes 740 which overlap catheter tip 750. Further, the order of steps wherein the diffusion holes 740 and catheter tip 750 are provided prior to lubricating the catheter tube body 714 avoids any impact on the catheter lube material, such as discoloration or burning of the lube material. This order of steps further allows the final diffusion hole geometry to be fully lubed and coated to minimize the impact of the diffusion hole's proximal edge during insertion.

The present invention may be embodied in other specific forms without departing from its structures, methods, or other essential characteristics as broadly described herein and claimed hereinafter. For example, the present method for manufacturing a peripheral catheter having a plurality of diffusion holes may include a catheter tube body which does not include an extruded stripe material. Further, the systems and methods of the present invention may be implemented in products and technologies outside of the infusion therapy arts. Therefore, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A peripheral catheter, comprising:
a tubular body member of a predetermined diameter and having a wall thickness, the tubular body member having a proximal end, a distal end and a lumen extending therebetween, the tubular body member further having a truncated length sufficient to access a peripheral vein of a patient, the distal end comprising a tapered tip, the tubular body member consisting of a first material;
an introducer needle positioned within the tubular body member prior to the peripheral catheter being inserted into the peripheral vein of the patient, the introducer needle having a sharpened distal tip that extends out the distal end of the tubular body member, the tapered tip of the tubular body member providing a transition from an outer surface of the introducer needle to the tubular body member to facilitate insertion of the peripheral catheter into the peripheral vein of the patient, the sharpened distal tip allowing the introducer needle to pierce through skin and the peripheral vein of the patient while the introducer needle is positioned within the tubular body member;
at least two stripes of a stiffening material embedded within the wall thickness of the tubular body, the stiffening material being different than the first material; and
a plurality of holes positioned on the tapered tip of the tubular body member, the plurality of holes being formed through the wall thickness of the tubular body member and in communication with the lumen to define an array of diffusion holes, the plurality of holes comprising a first set of holes disposed in a first annular ring, and a second set of holes disposed in a second annular ring, wherein the second set of holes is axially staggered from the first set of holes from about 15° to about 60°.

2. The peripheral catheter of claim 1, wherein the second set of holes is axially staggered from the first set of holes about 45°.

3. The peripheral catheter of claim 2, wherein the lumen further includes a first inner wall surface defining a first plane, and each staggered hole further includes a passage way having a second inner wall surface defining a second plane, wherein an orientation of the second plane is acute to an orientation of the first plane.

4. The peripheral catheter of claim 3, wherein the orientation of the second plane is about 45° relative to the orientation of the first plane.

5. The peripheral catheter of claim 3, wherein an orientation of the second lane relative to the first plane is from about 15° to about 75°.

6. The peripheral catheter of claim 1, wherein the truncated length is between 13 mm and 52 mm.

7. The peripheral catheter of claim 1, wherein the at least two stripes of stiffening material comprise a radiopaque material.

8. The peripheral catheter of claim 1, wherein the at least two stripes of stiffening material are helically extruded within the wall thickness of the tubular body.

9. The peripheral catheter of claim 1, wherein the stiffening material extends along the tapered tip.

10. The peripheral catheter of claim 1, further comprising:
a catheter adapter within which the proximal end of the tubular body member is secured, the catheter adapter including an inlet port;
a section of intravenous tubing having a distal end and a proximal end, the distal end being coupled to the inlet port; and
an adapter coupled to the proximal end of the section of intravenous tubing, the adapter being configured to allow an infusion system to be connected to the adapter.

11. A peripheral catheter, comprising:
a tubular body member of a predetermined diameter and having a wall thickness, the tubular body member having a proximal end, a distal end and a lumen extending therebetween, the lumen forming a first inner wall surface defining a first plane, the tubular body member further having a truncated length sufficient to access a peripheral vein of a patient, the distal end comprising a tapered tip, the tubular body member consisting of a first material;
an introducer needle positioned within the tubular body member prior to the peripheral catheter being inserted into the peripheral vein of the patient, the introducer needle having a sharpened distal tip that extends out the distal end of the tubular body member, the tapered tip of the tubular body member providing a transition from an outer surface of the introducer needle to the tubular body member to facilitate insertion of the peripheral catheter into the peripheral vein of the patient, the sharpened distal tip allowing the introducer needle to bypass skin and the peripheral vein of the patient while the introducer needle is positioned within the tubular body member;
a stiffening material coextruded with the first material to embed the stiffening material in a helical pattern within the wall thickness of the tubular body; and
a plurality of holes positioned on the tapered tip of the tubular body member, the plurality of holes being formed through the wall thickness of the tubular body member and in communication with the lumen to define an array of diffusion holes, each hole further including a passage way having a second inner wall surface defining a second plane, wherein an orientation of the second plane is acute to an orientation of the first plane, the plurality of holes comprising a first set of holes disposed in a first annular ring, and a second set of holes disposed in a second annular ring, wherein the second set of holes is axially staggered from the first set of holes from about 15° to about 60° to provide a staggered array of diffusion holes.

12. The peripheral catheter of claim 11, wherein the orientation of the second plane is about 45° relative to the orientation of the first plane.

13. The peripheral catheter of claim 11, wherein the stiffening material is radiopaque.

14. The peripheral catheter of claim 11, wherein the second set of holes is axially staggered from the first set of holes about 45°.

15. The peripheral catheter of claim 11, wherein the truncated length is between 13 mm and 52 mm.

16. The peripheral catheter of claim 11, wherein an inner surface of the tapered tip is also tapered to form a seal between the inner surface of the tapered tip and the outer surface of the introducer needle.

17. The peripheral catheter of claim 11, further comprising:
a catheter adapter within which the proximal end of the tubular body member is secured, the catheter adapter including an inlet port;

a section of intravenous tubing having a distal end and a proximal end, the distal end being coupled to the inlet port; and an adapter coupled to the proximal end of the section of intravenous tubing, the adapter being configured to allow an infusion system to be connected to the adapter.

18. The peripheral catheter of claim 11, wherein the stiffening material extends along the tapered tip.

19. The peripheral catheter of claim 11, further comprising an elongate gap disposed between an upstream hole and a downstream hole.

20. The peripheral catheter of claim 11, further comprising a third set of holes disposed in a third annular ring, wherein the third set of holes is axially staggered from the second set of holes, and the first set of holes is axially aligned with the third set of holes.

* * * * *